US007845230B2

(12) United States Patent
Oita et al.

(10) Patent No.: US 7,845,230 B2
(45) Date of Patent: Dec. 7, 2010

(54) CONCENTRATION SENSOR AND CONCENTRATION DETECTOR

(75) Inventors: Takeo Oita, Saitama (JP); Takehito Ishii, Saitama (JP)

(73) Assignee: Nihon Dempa Kogyo Co., Ltd., Tokyo (JP)

( * ) Notice: Subject to any disclaimer, the term of this patent is extended or adjusted under 35 U.S.C. 154(b) by 372 days.

(21) Appl. No.: 11/989,884

(22) PCT Filed: Aug. 2, 2006

(86) PCT No.: PCT/JP2006/315692

§ 371 (c)(1),
(2), (4) Date: Mar. 20, 2008

(87) PCT Pub. No.: WO2007/015575

PCT Pub. Date: Feb. 8, 2007

(65) Prior Publication Data
US 2010/0095750 A1    Apr. 22, 2010

(30) Foreign Application Priority Data
Aug. 3, 2005    (JP)    ............................. 2005-225699

(51) Int. Cl.
*G01H 11/08*    (2006.01)
(52) U.S. Cl. ........................................................ 73/579
(58) Field of Classification Search .................. 73/579
See application file for complete search history.

(56) References Cited
U.S. PATENT DOCUMENTS 4,991,283 A    2/1991    Johnson et al.

5,196,347 A    3/1993    Kaneko et al.
5,494,639 A    2/1996    Grzegorzewski
5,744,902 A  *  4/1998    Vig ............................. 310/360
5,892,143 A    4/1999    Namerikawa et al.
6,210,226 B1    4/2001    Zhu et al.
6,321,588 B1    11/2001    Bowers et al.
6,525,549 B1    2/2003    Poellmann
6,938,462 B2    9/2005    Jakoby et al.

(Continued)

FOREIGN PATENT DOCUMENTS

JP    61-85920    6/1986

(Continued)

*Primary Examiner*—Hezron Williams
*Assistant Examiner*—Rodney T Frank
(74) *Attorney, Agent, or Firm*—Jordan and Hamburg LLP

(57) ABSTRACT

In a concentration sensor using a piezoelectric piece, for instance, a quartz piece in which the natural frequency is varied by adsorption of a sensing target, the object of the present invention is to make the concentration sensor applicable to various fluids to be measured different in viscosity while restricting consumption of the oscillation energy due to interelectrode capacitance, and to be able to cope with plural types of concentration sensors while using a common oscillation circuit.

As a concrete means for solving the problem, an inductor is connected in parallel to the piezoelectric piece, and its inductance value is determined based on the relation between inductance values and oscillation loop gains in a gap between the inductance value Lmax canceling the interelectrode capacitance in a resonance frequency of the piezoelectric piece and the inductance value Lmin evaluated as the minimum value among the inductance values with which the piezoelectric piece can oscillate in a state of being immersed in a measuring fluid.

5 Claims, 4 Drawing Sheets

U.S. PATENT DOCUMENTS

| | | |
|---|---|---|
| 7,046,096 B2 | 5/2006 | Kobayashi |
| 7,055,377 B2 | 6/2006 | Paul et al. |
| 7,300,631 B2 * | 11/2007 | Miller et al. ............. 422/82.01 |
| 2004/0016297 A1 | 1/2004 | Paul et al. |
| 2004/0187580 A1 | 9/2004 | Nozaki |
| 2004/0233008 A1 | 11/2004 | Kobayashi |
| 2005/0052813 A1 | 3/2005 | Kobayashi |
| 2006/0141608 A1 | 6/2006 | Aastrup et al. |
| 2008/0047331 A1 | 2/2008 | Wakamatsu et al. |
| 2008/0129148 A1 | 6/2008 | Wakamatsu et al. |
| 2008/0134767 A1 | 6/2008 | Wakamatsu et al. |
| 2008/0156097 A1 | 7/2008 | Onishi et al. |

FOREIGN PATENT DOCUMENTS

| | | |
|---|---|---|
| JP | 1-244335 | 9/1989 |
| JP | 3-257346 | 11/1991 |
| JP | 4-1554 | 1/1992 |
| JP | 4-9744 | 1/1992 |
| JP | 5-5735 | 1/1993 |
| JP | 7-190916 | 7/1995 |
| JP | 9-145583 | 6/1997 |
| JP | 9-250936 | 9/1997 |
| JP | 10-142134 | 5/1998 |
| JP | 10-332463 | 12/1998 |
| JP | 11-183479 | 7/1999 |
| JP | 2000-338022 | 12/2000 |
| JP | 2001-83154 | 3/2001 |
| JP | 2001-099777 | 4/2001 |
| JP | 2001-201436 | 7/2001 |
| JP | 2002-148295 | 5/2002 |
| JP | 2002-243607 | 8/2002 |
| JP | 2004-205392 | 7/2004 |
| JP | 2004-264254 | 9/2004 |
| JP | 2004-304766 | 10/2004 |
| JP | 2005-43123 | 2/2005 |
| JP | 2005-515432 | 5/2005 |
| WO | WO 2004/085976 | 10/2004 |

* cited by examiner

CONCENTRATION SENSOR AND CONCENTRATION DETECTOR

TECHNICAL FIELD

The present invention relates to a technical field of an apparatus to detect the concentration of a sensing target or a target substance to be sensed, by using a piezoelectric piece such as a quartz piece which has an adsorbing layer to adsorb the sensing target on the surface and varies a natural frequency thereof when the sensing target is adsorbed, so as to detect the variation of the natural frequency of the piezoelectric piece.

BACKGROUND ART

A concentration detector using a quartz resonator is known as a method of sensing a very small amount of substance. The concentration detector makes up a quartz sensor (concentration sensor) by forming an adsorbing layer to adsorb a sensing target on the surface of the quartz resonator, so that the concentration of the sensing target is intended to determine by utilizing the property that when the sensing target is adhered to the adsorbing layer, the natural frequency thereof is varied according to the adhesion amount. More specifically, the main part is structured such that it includes an oscillation circuit connected to the quartz sensor and the measurement unit to determine the oscillation frequency of the oscillation circuit. Use of such a method has the merit that it is possible to measure even a substance in an extremely small amount because of its wide range of applicability, simplicity in device structure, and high sensitivity.

For instance, Patent Document 1 describes that the use of the quartz sensor during analyzing of a disease marker substance contained in blood, urine, and so on is an effective method substituting an immuno-latex kit which requires an expensive large automatic analyzer. When the quartz sensor is used as a biosensor in this manner, the adsorbing layer composed of an antibody which induces an antibody-antigen reaction against a sensing target substance is formed in a quartz resonator.

When the quartz sensor is immersed in a liquid, the equivalent series resistance value of the quartz piece increases to the level of, for instance, several hundred Ω, and if the liquid is pure water, it shows an increase of about 150Ω. Therefore, it is designed to give a large amount of energy to the quartz piece. However, the interelectrode capacitance C0 of the quartz resonator consumes this energy, which results in energy loss. Accordingly, cancellation of the interelectrode capacitance C0 is necessary on the oscillation circuit side. However, even the interelectrode capacitance C0 of a certain quartz sensor is cancelled by an inductor on the oscillation circuit side, when the quartz sensor is changed to another quartz sensor having a different interelectrode capacitance C0, it is necessary to adjust the inductance value of the inductor on the oscillation circuit side every time. This operation requires complicated and time-consuming work such that the interelectrode capacitance C0 is measured for every type of quartz sensors with an LCR meter or the like on the user side to exchange with an inductor having a proper inductance value after having calculated based on the measurement value. Although it is also conceivable to prepare an oscillation circuit corresponding to the type of the quartz sensor to be used instead of exchanging the inductor, it requires an expensive system.

Patent Document 2 describes necessity of canceling the interelectrode capacitance by connecting inductance to a quartz resonator in parallel, but the invention is in a field of a completely different technology, and is not intended to solve the problem of the present invention.

Patent Document 1
    Japanese Patent Application Laid-open No. 2001-83154: Column 0002, and 0004.

Patent Document 2
    Japanese Utility Model Laid-open No. Sho 61-85920: FIG. 1

DISCLOSURE OF THE INVENTION

The present invention has been achieved under such a circumstance, and an object of the present invention is to provide a technology to cope with different types of concentration sensors using a common oscillation circuit in a concentration sensor using a piezoelectric piece which varies the natural frequency thereof due to adsorption of a sensing target, and a concentration detector using the above-described sensor.

A concentration sensor of the present invention, detachably connected to a measurement device main unit provided with an oscillation circuit to detect the concentration of a sensing target includes:

a piezoelectric resonator including a piezoelectric piece having an adsorbing layer to adsorb a sensing target and varying the natural frequency thereof by adsorption of the sensing target, and electrodes respectively provided on both surfaces of the piezoelectric piece; and an inductor connected to the above-described piezoelectric resonator in parallel.

A concentration sensor of another invention, detachably connected to a measurement device main unit provided with an oscillation circuit to detect the concentration of a sensing target includes:

a circuit board detachably connected to the above-described measurement device main unit, and provided with a pair of conductive paths, the one end thereof serving as a terminal connected to the terminal of the measurement device main unit;

a piezoelectric resonator provided on the above-described circuit board including a piezoelectric piece having an adsorbing layer for adsorbing a sensing target formed thereon and varying the natural frequency by adsorption of the sensing target, and electrodes respectively provided on both surfaces of the piezoelectric piece;

an upper lid case forming a housing space for a fluid between the piezoelectric resonator and provided with a pouring opening for the fluid connecting through the housing space; and an inductor connected in parallel to the above-described piezoelectric resonator, and provided between a pair of conductive paths of the above-described circuit board.

It is preferable to set the inductance value of the above-described inductor to be ±20% to the median value which is the mean value between the inductance value canceling the interelectrode capacitance of the piezoelectric resonator by a resonance frequency of the above-described piezoelectric resonator and the minimum value of the inductance able to oscillate the piezoelectric resonator when immersed in the fluid to be measured.

It is also preferable to adopt a structure such that an opening is provided to the above-described circuit board, and the bottom side of the above-described piezoelectric resonator faces a recess formed on the above-described opening.

A concentration detector of the present invention includes:
the above-described concentration sensor;
a detachable terminal of the concentration sensor; and
a measuring unit for determining the concentration of a sensing target based on the oscillation circuit for oscillating the above-described piezoelectric piece and the oscillation output from the oscillation circuit.

According to the present invention, since the inductor is connected in parallel to the piezoelectric piece forming the concentration sensor, by setting the inductance value to a suitable value, the piezoelectric piece does not stop oscillation in various fluids to be measured, which is different in viscosity (sample fluid) while restricting consumption of oscillation energy due to the interelectrode capacitance. Furthermore, since the concentration sensor is provided with the inductor, adjustment of the oscillation circuit side to various concentration sensors is not required, in other words, it is applicable to various concentration sensors though it is a common oscillation circuit. Therefore, it becomes unnecessary to perform the complicated and time-consuming work of adjusting the oscillation circuit side on the user side.

BEST MODE FOR CARRYING OUT THE INVENTION

Figure 1:
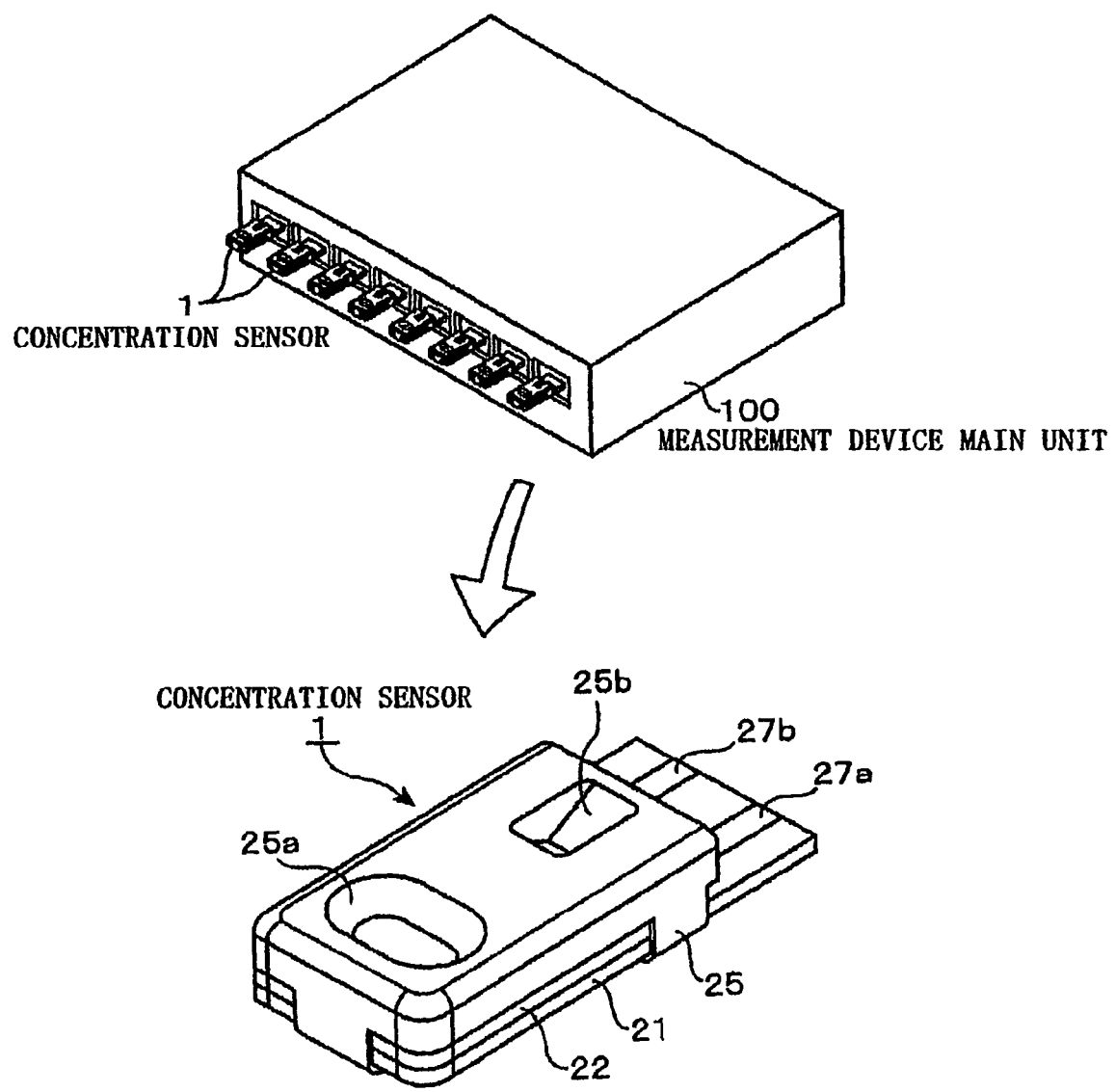
FIG. 1 is a perspective view showing an outside appearance of an embodiment of a concentration detector including a concentration sensor relating to the present invention.
Figure 2:
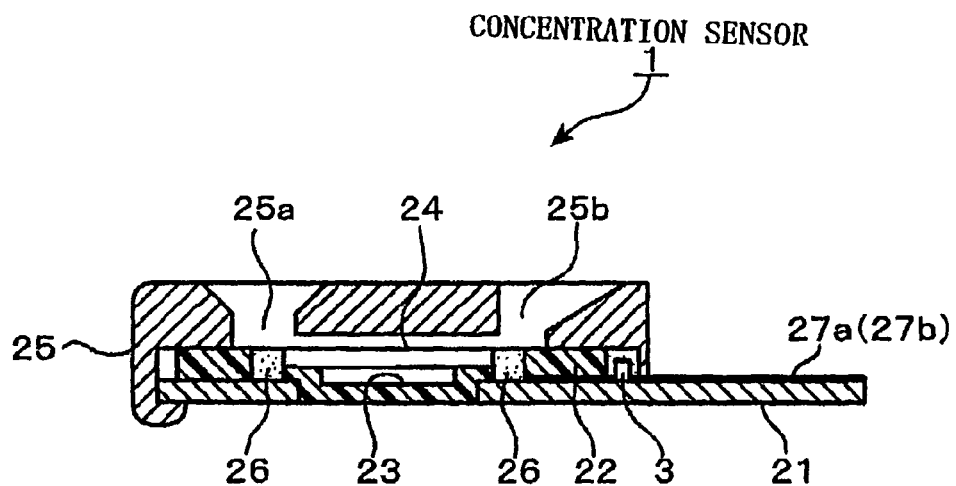
FIG. 2 is a vertical cross section showing the concentration sensor used in the above-described embodiment.

Hereinafter, an embodiment of a concentration detector relating to the present invention will be explained. A whole structure of the concentration detector will be explained briefly first. The concentration detector is provided with a plurality of, for instance, 8 pieces of concentration sensors (quartz sensor) 1 and a measurement device main unit 100 to which these concentration sensors 1 are detachably installed, as shown in FIG. 1. The concentration sensors 1 is provided with a circuit board, for instance, a printed circuit board 21 as shown in FIGS. 1 and 2, and an opening 23a is formed on the printed circuit board 21. A rubber sheet 22 is overlaid on the front surface side of the above-described printed circuit board 21, and a recess 23 is arranged on the rubber sheet 22. The part corresponding to the recess 23 protrudes on the bottom surface side of the rubber sheet 22, and its protruded part is fitted into the opening 23. A quartz resonator 24 being a piezoelectric resonator is provided to cover the above-described recess 23. That is, one surface side (bottom surface side) of the quartz resonator 24 faces toward the above-described opening 23, and the bottom surface side of the quartz resonator 24 is made to be an airtight space owing to the above-described recess 23, and thus, a Langevin-type concentration sensor is built up.

Furthermore, an upper lid case 25 is installed from above the rubber sheet 22. The upper lid case 25 includes a pouring opening 25a for pouring a sample solution which is a fluid to be measured and an observation opening 25b for observing the sample solution. The sample solution is poured from the pouring opening 25a so that the sample solution is filled in a space on the upper surface side of the quartz resonator 24 (the quartz piece is immersed in the sample solution).

It should be noted that the structure of the concentration sensor 1 may be such that the quartz resonator 24 is installed on the surface of the printed circuit board 21 so as to cover the above-described opening 23a and the surroundings of the quartz resonator 24 is pressed with the rubber sheet 22.

Figure 3:
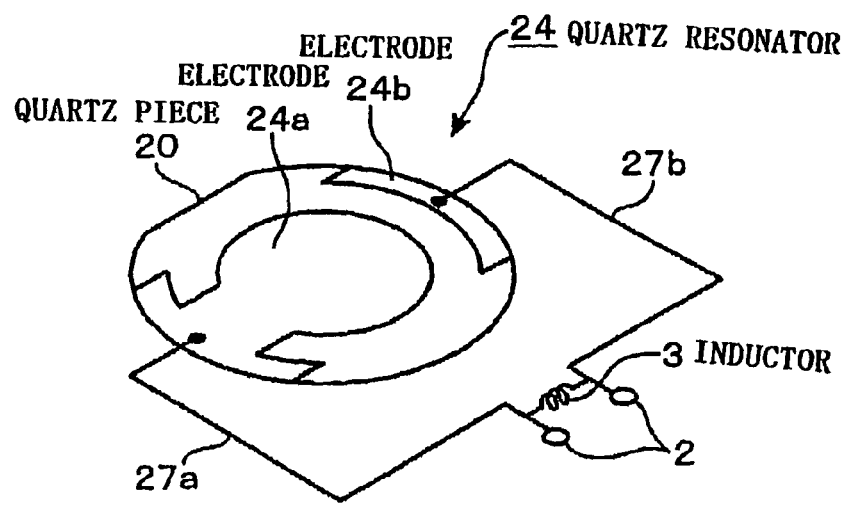
FIG. 3 is an explanatory view showing a quartz resonator and wiring in the surrounding area thereof used in the above-described embodiment.

The quartz resonator 24 includes respective electrodes 24a and 24b on both surfaces of a quartz piece 20, for instance, in a circular shape (the electrode 24b on the back surface side is formed to be continuous to the peripheral part on the front surface side) as shown in FIG. 3, and these electrodes 24a and 24b are electrically connected respectively to printed circuits 27a and 27b which are a pair of conductive paths arranged on the substrate 21 via a conductive adhesive 26. An adsorbing layer (not shown) for adsorbing a sensing target is formed on one surface of the quartz resonator 24, for instance, on the front surface of the electrode 24a.

Figure 4:
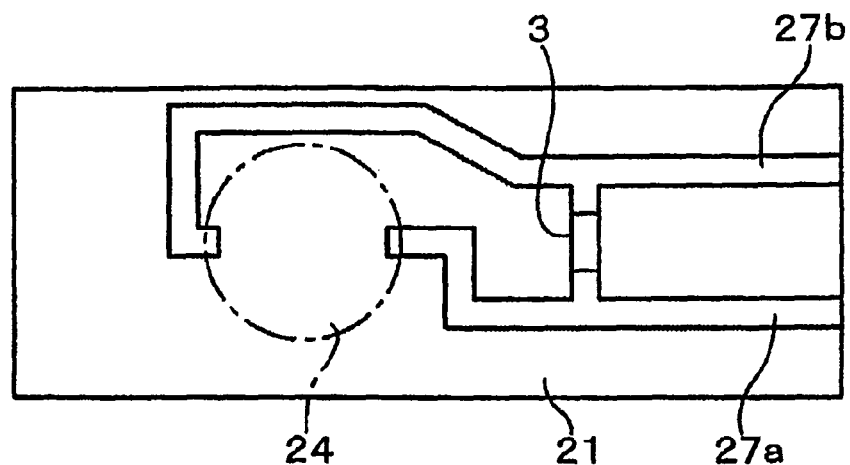
FIG. 4 is a plan view showing the concentration sensor and circuit of the above embodiment.

Further as shown in FIGS. 2 to 4, an inductor 3 composed of, for instance, discrete parts is connected between the printed circuits 27a and 27b, and the inductor 3 is installed on the circuit board 21 and covered with the upper lid case 25. Note that the inductor 3 may be formed using a print pattern.

A method of determining the inductance value of the inductor 3 will be explained. Since the concentration sensor detects the concentration of a sensing substance in a fluid to be measured, for instance, in a solution to be measured, on the basis of the variation amount of oscillation frequency according to the mass of the sensing substance adhered to a peculiar adsorbing film, it must not stop oscillation in the fluid to be measured. However, according to an experiment, when the quartz piece 20 is immersed in a fluid sample, the equivalent series resistance R1 of the quartz piece 20 is drastically increased. For instance, in the case of driving the quartz piece 20 at 31 MHz, it increases to as high as 500Ω, though it is only 10Ω when the quartz piece 20 is placed in the air, which means that it becomes a state to be extremely difficult for oscillation.

In order to solve this problem, the present invention intends to perform prevention of the stop oscillation by controlling the phase of the quartz piece 20 by connecting the inductor 3 in parallel to the quartz piece 20. However, when the inductance value of the inductor 3 is set to a value to cancel the interelectrode capacitance C0, the following inconveniences take place.

Figure 5:
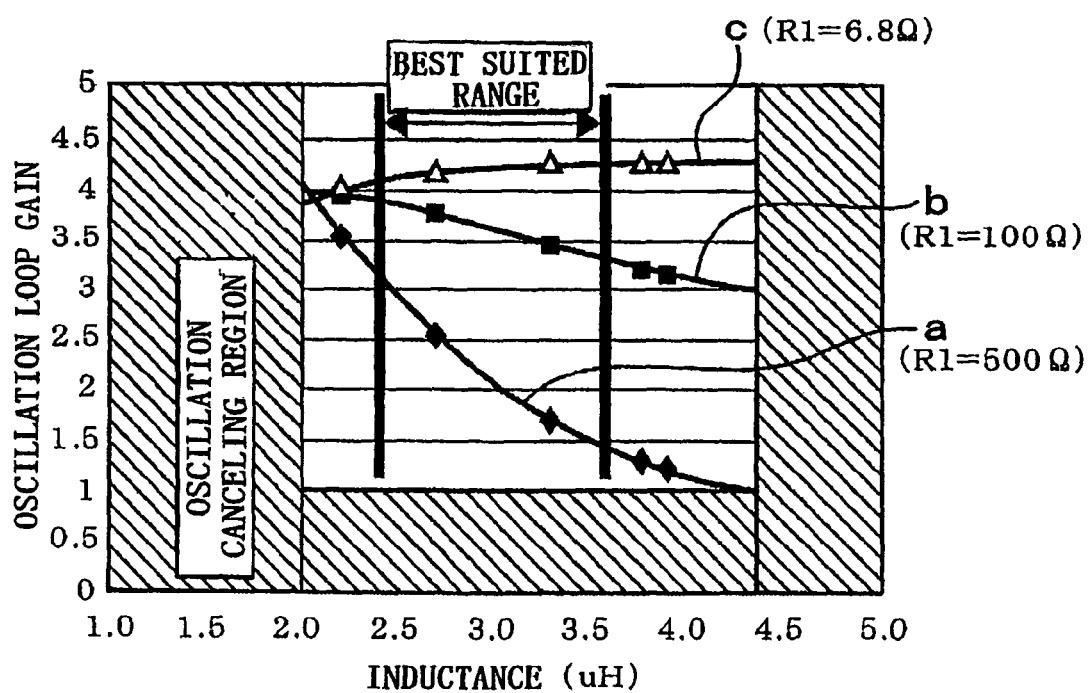
FIG. 5 is an explanatory view showing data for determining the inductance value of an inductor provided in the concentration sensor used in the above embodiment.

FIG. 5 is a relation diagram of inductance values and loop gains of the inductor 3 determined as such by calculation. The equivalent series resistance R1 of the quartz piece 3 is determined in these three settings of 6.8Ω, 100Ω, and 500Ω. The reason for setting the equivalent series resistance R1 to these 3 values is to check how the relation between the inductance value and the oscillation loop gain varies using the equivalent series resistance R1 as a parameter, and to grasp the above-described relation under hard conditions in which a solution having the highest viscosity among the solutions measured with the concentration sensor is assumed and the equivalent series resistance R1 is estimated to be 500Ω when the quartz piece 3 is immersed in the solution. In this example, since the resonance frequency Fr of the quartz piece 20 is 31 MHz, the interelectrode capacitance C0 is 7.05 pF, the inductance value with which the interelectrode capacitance C0 is cancelled at the series resonance point Fr of the quartz piece 20 is about 3.8 μH. This inductance value is expressed to be $1/(C0 \cdot \omega^2)$ where the angular velocity of the above-described resonance frequency Fr is ω.

When the equivalent series resistance R1 is 500Ω, however, the inductance value of 3.8 μH is not suitable because the oscillation loop gain is close to 1. When setting an inductance value, since this inductance value is never exceeded, it is called Lmax (the largest value permissible) here.

On the other hand, when the inductance value is made smaller for any equivalent series resistance R1, it stops oscillation because it loses the ability to cancel the effect of the interelectrode capacitance C0. The limit value thereof is about 2.0 μH. The method of determining this limit value 2.0 μH will be described here. The conditions to activate an oscillation circuit are such that when a signal goes once through around the circuit to be an intended oscillation loop, the gain should be one or more, and the phase should be an integral multiple of 360 degrees. The minimum of the inductance value satisfying the latter condition, i.e. phase condition is 2.0 μH.

A concrete example of the method of determining these conditions will be described as follows. The intended oscillation loop is cut at a point to form contact points A and B. Then, a signal source of the small signal so small as to make the circuit operate linearly is connected to the contact point A so as to drive the circuit. At this time, the signal at the contact point B is observed, and the ratio of the signals at the contact points A and B is taken. Then, the gain and phase at the time of making a circuit go once through around the oscillation loop are measured. Accordingly, it is possible to obtain the minimum inductance value at which the phase condition cannot be satisfied anymore when the inductance value of the inductor is varied. Then, when the gains are plotted using inductance values of the inductor connected in parallel to the quartz resonator as a parameter, the result shown in FIG. 5 is obtained.

The above-described inductance value 2.0 μH is the inductance value Lmin evaluated to be the minimum inductance value possible to oscillate in a state that the quartz piece 20 is immersed in a fluid to be measured. As is clear from FIG. 5, it is not appropriate for the concentration sensor to determine the above-described inductance value to Lmax with which the interelectrode capacitance C0 is cancelled. On the contrary, it is suitable to determine the value not too close to the oscillation canceling region but the value with which a sufficient oscillation loop gain can be obtained from the relation of the inductance values and oscillation loop gains between the inductance values Lmin and Lmax when immersing the quartz piece 20 in the measuring fluid. In this example, the range from 2.3 μH to 3.5 μH, which is ±20% around the mean value 2.9 μH between the inductance values Lmin and Lmax is handled as the best suited range of the inductance value of the inductor 3. When the inductance value is determined in this way, the characteristics of the product is stabilized in mass production of the concentration sensor.

Since the greater the magnitude of the equivalent series resistance R1, the more the degree of lowering of the oscillation loop gain accompanying increase in the inductance value of the inductor 3, the inductance values Lmin and Lmax are determined for the equivalent series resistance R1 at the time when the viscosity is highest among the fluids to be measured in which the concentration sensor is used, for instance, if the sensor is a gas-liquid dual purpose sensor, at the time when the viscosity is highest among the solutions to be measured, and the most suitable value for the inductance of the inductor 3 may be determined based on the relation between the inductance value and the oscillation loop gain during thereof.

Figure 6:
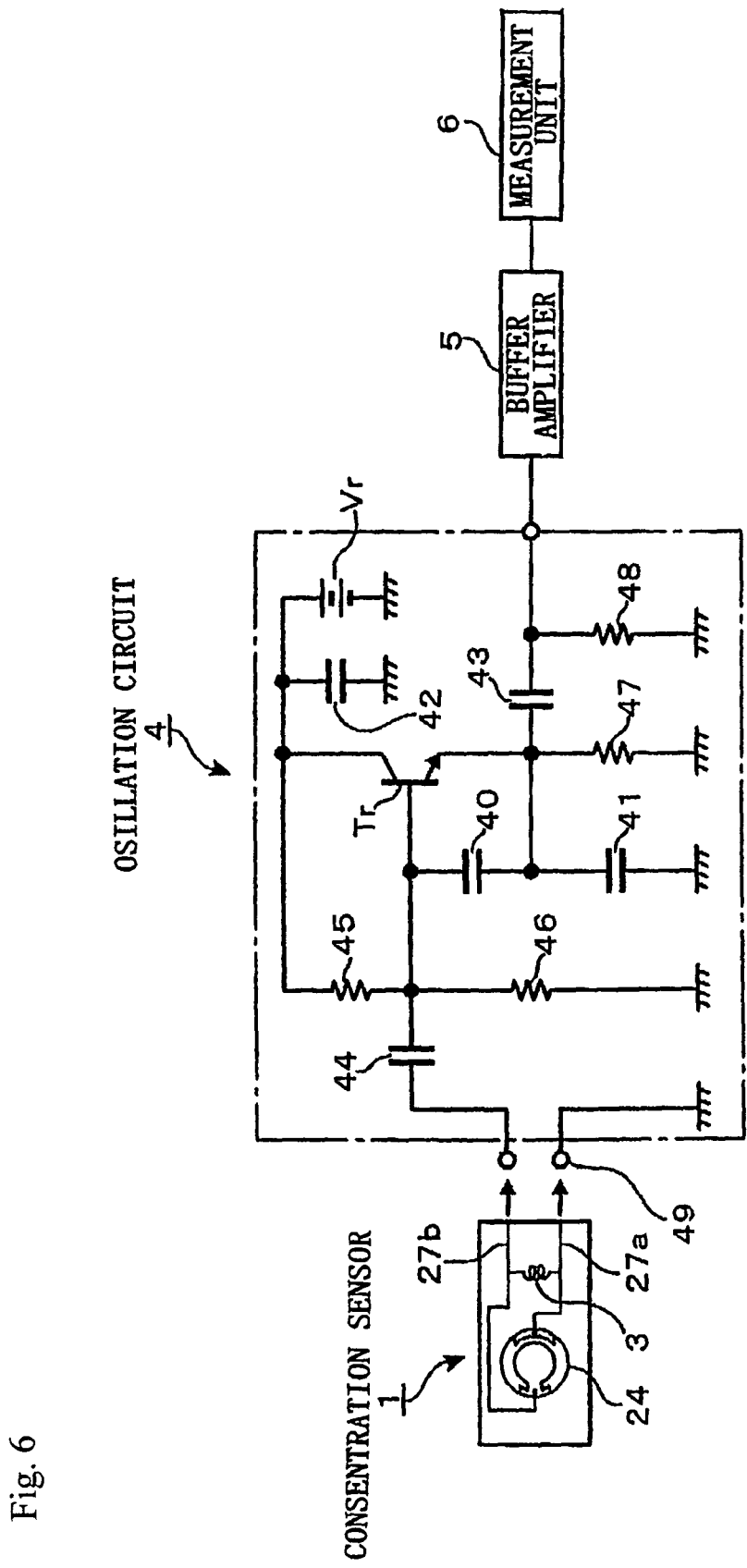
FIG. 6 is a block circuit diagram showing the concentration detector in the above embodiment.

Next, the circuit inside the measurement device main unit 100 will be briefly explained using FIG. 6. In FIG. 6, 4 designates an oscillation circuit to oscillate the quartz resonator 24 of the concentration sensor 1, and a measurement unit 6 is connected to the latter part of the oscillation circuit 4 via a buffer amplifier 5. The oscillation circuit 4 is structured as a Colpitts type oscillation circuit, Tr is a transistor used as an oscillation amplification device, 40 and 41 are capacitors constituting split capacitive elements, and Vc designates a supply source. As for other parts, 42 to 44 are capacitors, 45 to 48 are resistors. 49 designates a terminal unit which the concentration sensor 1 is detachably connected to, provided in the measurement device main unit 100 shown in FIG. 1.

The measurement unit 6 includes a measurement device to determine the signal relating to the frequency of the oscillation output of the oscillation circuit 4 such as a frequency counter, and a microprocessing unit for computing the variation in the count number.

It should be noted that this example takes an eight-channel structure having 8 pieces of the concentration sensor 1 attached thereto, in which the circuit shown in FIG. 6 is provided with 8 channels, and the output of each channel is switched over to be connected to the measurement unit 6.

Operation of this embodiment will be explained next. First, the concentration sensor 1 (refer to FIG. 1) is plugged into the measurement device main unit 100, a solution not containing a sensing target is filled in the concentration sensor 1 and the quartz resonator 24 is oscillated to determine, for example, a blank value. The solution may be pure water or other solutions. The oscillation output in the oscillation circuit 3 is inputted into the measuring unit 6 via the buffer amplifier 5, and for instance, the frequency of an oscillation output is measured. Then, a solution to be measured which is a sample to conduct detection of a sensing target is poured into the concentration sensor 1, the variation of the oscillation frequency caused by pouring the measuring solution is measured by the measuring unit 6, and the concentration of the sensing target is detected based on the variation from, for instance, a calibration curve prepared in advance.

According to the above-described embodiment, the inductor 3 is connected in parallel to the quartz piece 20, the value Lmin which is evaluated as the minimum value among the inductance values, at which the quartz piece 20 can be oscillated in a state of being immersed in a measuring solution, and the value Lmax canceling the interelectrode capacitance C0 are determined, an inductance value is suitably determined between the values Lmin and Lmax, considering the relation between the inductance value and the oscillation loop gain. Therefore, it is possible to reduce consumption of the oscillation energy due to the interelectrode capacitance C0 and it never stops oscillation even when various measuring fluids different in viscosity are used. In addition, since the concentration sensor 1 attachable to and detachable from the measurement device main unit is provided with the inductor 3, it is possible to conduct suitable measurement by using the concentration sensor 1 provided with the inductor 3 matching to the viscosity of a sample fluid. Accordingly, since no adjustment is required on the oscillation circuit 4 side for various concentration sensors, in other words, though it is a common oscillation circuit 4, it is applicable to the various concentration sensors. Therefore, it is not necessary to perform the complicated and time-consuming work of adjusting the oscillation circuit on the user side.

Further, when using the above-described concentration sensor 1, since the concentration sensor 1 can be replaced by detaching and attaching the printed circuit 21 from and to the measurement device main unit 100, replacement work is easy. In addition, since a Langevin-type concentration sensor is structured by forming an airtight space on the bottom surface side of the quartz resonator 24 utilizing the opening 23*a* prepared in the printed circuit 21, the structure to form the above-described airtight space is simple.

Note that the concentration sensor of the present invention is not limited to determination of the concentration of the sensing target, but it also includes a sensor for detecting the presence or absence of the sensing target.

The invention claimed is:

1. A concentration sensor detachably connected to a measurement device main unit provided with an oscillation circuit to detect the concentration of a sensing target, comprising:
   a piezoelectric resonator including a piezoelectric piece having an adsorbing layer to adsorb a sensing target and varying the natural frequency thereof by adsorption of the sensing target, and electrodes respectively provided on both surfaces of the piezoelectric piece; and
   an inductor connected in parallel to said piezoelectric resonator.

2. The concentration sensor according to claim 1, wherein the inductance value of said inductor is set to be ±20% to the median value which is the mean value between the inductance value canceling the interelectrode capacitance of the piezoelectric resonator by a resonance frequency of said piezoelectric resonator and the minimum value of the inductance able to oscillate the piezoelectric resonator when immersed in the fluid to be measured.

3. The concentration sensor according to claim 1, wherein said circuit board is provided with an opening, and the bottom side of said piezoelectric resonator faces a recess formed on said opening.

4. A concentration sensor, detachably connected to a measurement device main unit provided with an oscillation circuit to detect the concentration of a sensing target, comprising:
   a circuit board detachably connected to said measurement device main unit, and provided with a pair of conductive paths, the one end thereof serving as a terminal connected to the terminal of the measurement device main unit;
   a piezoelectric resonator provided on said circuit board, including a piezoelectric piece having an adsorbing layer for adsorbing a sensing target, varying the natural frequency by adsorption of the sensing target and electrodes respectively provided on both surfaces of the piezoelectric piece;
   an upper lid case forming a housing space for a fluid between said piezoelectric resonator and provided with a pouring opening for the fluid connecting through the housing space; and
   an inductor connected in parallel to said piezoelectric resonator, and provided between a pair of conductive paths of the circuit board.

5. A concentration detector, comprising:
   the concentration sensor according to claims 1, 4, 2 or 3;
   a terminal unit to which the concentration sensor is detachably connected; and
   a measuring unit for determining the concentration of a sensing target based on the oscillation circuit for oscillating said piezoelectric resonator and the oscillation output from the oscillation circuit.

* * * * *